United States Patent

Giesselmann et al.

[11] 4,089,887
[45] May 16, 1978

[54] PROCESS FOR THE PRODUCTION OF ISOTHIOCYANATES

[75] Inventors: Günter Giesselmann, Heusenstamm; Gerd Schreyer; Rudolf Vanheertum, both of Hanau, all of Germany

[73] Assignee: Deutsche Gold- und Silber-Scheideanstalt Vormals Roessler, Frankfurt, Germany

[21] Appl. No.: 762,792

[22] Filed: Jan. 25, 1977

[30] Foreign Application Priority Data

Jan. 30, 1976 Germany .............................. 2603508

[51] Int. Cl.² .................. C07C 161/04; C07D 211/98; C07D 277/38
[52] U.S. Cl. .............................. 260/454; 260/294.8 E; 260/306.8 R
[58] Field of Search .......... 260/454, 294.8 E, 306.8 R

[56] References Cited

U.S. PATENT DOCUMENTS

| | | | |
|---|---|---|---|
| 2,338,902 | 1/1944 | Claudin | 260/454 |
| 3,787,472 | 1/1974 | Giesselmann et al. | 260/454 |

Primary Examiner—Elbert L. Roberts
Assistant Examiner—Robert C. Whittenbaugh
Attorney, Agent, or Firm—Cushman, Darby & Cushman

[57] ABSTRACT

Isothiocyanates of the formula (I)

$$R-N=C=S \qquad (I)$$

in which R is a straight or branched alkyl group with 1 to 18 carbon atoms, preferably methyl, and wherein the alkyl group can be substituted once or more by —OH, —OR¹ or —SR¹ and where R¹ is an alkyl group of 1 to 6 carbon atoms or R is cycloalkyl with 3 to 8 carbon atoms, benzyl or phenyl in which the aromatic nucleus can be substituted once or more by a chlorine atom, a bromine atom, a hydroxyl group, or —R¹, —OR¹ or —SR¹ or R is a pyridyl or thiazolyl group prepared by reacting (1) a dithiocarbamate of the general formula (II)

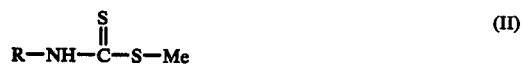

where R is as defined above and Me is an alkali atom, one valence of an alkaline earth metal atom or the ammonium group whose hydrogen atoms can be substituted by R with (2) a cyanogen halide, preferably cyanogen chloride, in the presence of water. There is employed one mole of a dithiocarbamate of formula II as a 5 to 50 weight % aqueous solution in the presence of an inert organic solvent which is not miscible with water, and preferably in the presence of a base at a temperature from about −10° C to about +50° C, preferably between 0° C and 25° C. There is employed at least one mole of cyanogen chloride per mole of dithiocarbamate. The isothiocyanate produced is isolated from the organic phase.

18 Claims, No Drawings

PROCESS FOR THE PRODUCTION OF ISOTHIOCYANATES

BACKGROUND OF THE INVENTION

It is known to prepare isothiocyanates by oxidizing N-monosubstituted dithiocarbamates with concentrated hydrogen peroxide, see German Pat. No. 2,105,473 and related Giesselmann U.S. Pat. 3,787,472. According to this process there are obtained alkylisothiocyanic acid esters in a purity of 98% and in high yields. However, important disadvantages of this process are that only alkyl derivatives are accessible and that relatively high hydrogen peroxide concentrations must be used.

Furthermore, it is known to produce isothiocyanates by reaction of N-monosubstituted dithiocarbamates with cyanogen chloride in aqueous solution, see Claudin U.S. Pat. No. 2,338,902. However, according to this process the lower alkyl isothiocyanates can only be obtained in yields of about 65 to 70%. Besides, as by-products considerable amounts of water insoluble thiocyanogen compounds are formed which increased the difficulty of the working up process.

It is the objective of the invention to develop a new process for producing isothiocyanates which do not have the above stated disadvantages.

SUMMARY OF THE INVENTION

It has now been found that there can be produced isothiocyanates of the general formula (I)

R—N=C=S     (I)

where R is a straight or branched chain alkyl group with 1 to 18 carbon atoms, preferably methyl and where the alkyl group can also be substituted with one or more —OH, —OR$^1$ or —SR$^1$ groups wherein R$^1$ is alkyl of 1 to 6 carbon atoms, or R can be cycloalkyl with 3 to 8 carbon atoms or R can be benzyl or phenyl and wherein the aromatic nucleus of the benzyl or phenyl group can be substituted with one or more chlorine atoms, bromine atoms, hydroxyl groups, phenoxy groups or with the above-mentioned —R$^1$, —OR$^1$ or —SR$^1$ groups, or R can be a pyridyl or thiazolyl group by reaction of (1) a dithiocarbamate of the general formula (II)

$$\text{R—NH—}\overset{\text{S}}{\underset{\|}{\text{C}}}\text{—S—Me}$$     (II)

in which R is as defined above and Me is an alkali atom, e.g., sodium or potassium, a valence of an alkaline earth metal atom, e.g., calcium, barium, strontium or magnesium, or is the ammonium group or an ammonium group where hydrogen atoms can be replaced by the group R with (2) a cyanogen halide, e.g., cyanogen chloride or cyanogen bromide (with cyanogen chloride being the preferred cyanogen halide) in the presence of water when there is employed one mole of a dithiocarbamate of general formula (II) as a 5 to 50% by weight aqueous solution in the presence of an inert, water-immiscible organic solvent, preferably in the presence of a base at a temperature of about −10° C to about 50° C, preferably between about 0° C and 25° C with at least one mole of a cyanogen halide, preferably cyanogen chloride and the isothiocyanate obtained is isolated in known manner from the organic phase.

According to this process which employs a two phase system the isocyanate is obtained in yields of above 90% and in a purity of more than 99%.

In carrying out the process one can proceed by employing dithiocarbamates of general formula (II) as such, said dithiocarbamate having been produced in known manner. However, it also is possible to start with the solution for producing the dithiocarbamate. To this aqueous solution there is added the water immiscible organic solvent for the isothiocyanate produced. The upper limit on the amount of water immiscible organic solvent employed is not critical. As the lower limit there is brought in that amount of solvent which makes it possible to bring into solution the isothiocyanate formed during the reaction.

It is advantageous to use a slight excess of cyanogen halide, preferably cyanogen chloride. Preferably there is used a 5 to 10% excess of the cyanogen halide.

The reaction between the dithiocarbamate and cyanogen halide is exothermic. The reaction temperature is maintained between −10° C and +50° C, preferably between 0° and 25° C. Depending on the temperature maintained, the cyanogen halide can be introduced into the reaction mixture as a liquid or gas. On the other hand, it is also possible to have the cyanogen halide present in liquid form or dissolved in the organic solvent or to meter it in dissolved form.

During the reaction there is formed isothiocyanate, the metal halide and thiocyanic acid.

It is advantageous to work in the presence of a base, for example, ammonium hydroxide or an alkali metal hydroxide, e.g., potassium hydroxide or especailly sodium hydroxide. By addition of a base there is formed in the reaction besides the isothiocyanate the above described halide not only the thiocyanic acid but, depending on the amount of base added, the corresponding thiocyanate. If one or more equivalent of base is added per equivalent of starting dithiocarbamate at the end of the reaction there is no longer present any free thiocyanic acid. The base also can in a given case be fed in during the reaction. An advantage of this reaction procedure is that only unequivocal thiocyanogen compounds, namely, thiocyanates, are formed. They are present at the end of the reaction together with the halides dissolved in the aqueous phase, while the isothiocyanate is dissolved in the organic phase. Insofar as this solution is not to be further used as such, the isolation of the isocyanate takes place in known manner, for example, by fractional distillation or by crystallization. The halide and thiocyanate can be isolated from the aqueous phase in known manner.

Examples of inert solvents which can be used with advantage within the space of the inventions include hydrocarbons, e.g., hexane, octane, benzene, toluene, cyclohexane, chlorinated hydrocarbons, e.g., methylene chloride, chloroform, carbon tetrachloride, ethylene dichloride, water insoluble ketones, e.g., 4-heptanone, 4-octanone and cyclopentanone, water insoluble ethers, e.g., ethyl isobutyl ether and ethyl heptyl ether, water insoluble esters, e.g., octyl acetate and hexyl propionate, and nitrobenzene. The preferred solvent is methylene chloride.

The alkyl isothiocyanic acid esters which can be produced by this process (the methyl derivative being particularly preferred) can be used as starting materials for the synthesis of other compounds, for example, substituted thioureas. Besides, they exhibit a biological activity and can be used particularly as nematocides, fungicides and bactericides.

For example, there can be produced according to this process methyl isothiocyanate, ethyl isothiocyanate, n-butyl isothiocyanate, cyclohexyl isothiocyanate, phenyl isothiocyanate, t-butyl isothiocyanate, 2-methoxyethyl isothiocyanate, cyclopentyl isothiocyanate, p-methoxyphenyl isothiocyanate, p-phenoxyphenyl isothiocyanate, 3-methylphenyl isothiocyanate, 3-chlorophenyl isothiocyanate, benzyl isothiocyanate, 4-methoxybenzyl isothiocyanate, 2-isothiocyanato pyridine, 2-isothiocyanatothiazole, decyl isothiocyanate, hexyl isothiocyanate, dodecyl isothiocyanate, octadecyl isothiocyanate, 2-hexoxyethyl isothiocyanate, 2-ethoxypropyl isothiocyanate, hydroxyethyl isothiocyanate, 2-hydroxypropyl isothiocyanate, methylthioethyl isothiocyanate, hexylthioethyl isothiocyanate, cyclopropyl isothiocyanate, 4-bromophenyl isothiocyanate, 2,6-dichlorophenyl isothiocyanate, 3-hydroxyphenyl isothiocyanate, 4-hydroxyphenyl isothiocyanate, 4-methylphenyl isothiocyanate, 3,5-dimethylphenyl isothiocyanate, 4-t-butylphenyl isothiocyanate, 3-methyl-4-chlorophenyl isothiocyanate, cyclooctyl isothiocyanate, o-hexoxyphenyl isothiocyanate, p-methylthiophenyl isothiocyanate.

When the dithiocarbamate starting material is formed in situ the starting aqueous solution can include the base, e.g., sodium hydroxide, potassium hydroxide, ammonium hydroxide, calcium hydroxide or barium hydroxide, carbon disulfide and the appropriate amine, e.g., methyl amine, ethyl amine, propyl amine, isopropyl amine, t-butyl amine, sec.butyl amine, n-butyl amine, decyl amine, dodecyl amine, hexadecyl amine, octadecyl amine, ethanolamine, propanolamine, 2-hydroxypropylamine, aniline, o-toluidine, m-toluidine, p-toluidine, methoxyethyl amine, ethoxyethyl amine, hexoxyethyl amine, ethoxypropyl amine, cyclohexyl amine, cyclooctyl amine, cyclopropyl amine, cyclopentyl amine, p-methoxy aniline, p-phenoxy aniline, p-ethoxy aniline, p-hexoxy aniline, 3-chloroaniline, 4-chloroaniline, 4-bromoaniline, 2,6-dichloroaniline, 3,4-dichloroaniline, benzyl amine, 4-methoxybenzyl amine, 4-chlorobenzyl amine, methylthioethyl amine, hexylthioethyl amine, 3-hydroxy aniline, 4-hydroxy aniline, 3,5-dimethyl aniline, 4-t-butyl aniline, 3-hexyl aniline, 3-methyl-4-chloroaniline, o-hexoxy aniline, p-methylthio aniline.

If the dithiocarbamate itself is employed as the starting material there can be used for example N-methyl sodium dithiocarbamate, N-ethyl sodium dithiocarbamate, N-hexyl sodium dithiocarbamate, N-octadecyl sodium dithiocarbamate, N-cyclohexyl sodium dithiocarbamate, N-2-methoxyethyl sodium dithiocarbamate, N-4-chlorophenyl sodium dithiocarbamate, N-4-methoxyphenyl sodium dithiocarbamate as well as salts with other bases, e.g., N-methyl potassium dithiocarbamate, N-ethyl potassium dithiocarbamate, N-methyl ammonium dithiocarbamate and N-methyl calcium dithiocarbamate.

Unless otherwise indicated all parts and percentages are by weight.

The process can comprise, consist essentially of or consist of the steps set forth and the materials can comprise consist essentially of or consist of those set forth.

DESCRIPTION OF THE PREFERRED EMBODIMENTS

EXAMPLE 1

In the course of one hour there were reacted in known manner 0.447 mole of 40% aqueous methyl amine with 0.447 mole of carbon disulfide and 0.447 mole of sodium hydroxide (40% solution in water) to form an aqueous N-methyl sodium dithiocarbamate solution. To this solution there were added 398 grams of carbon tetrachloride and there were introduced with stirring within 30 minutes 0.563 mole of gaseous cyanogen chloride. The mixture was cooled to such an extent that the reaction temperature was about 11° C. After the reaction the organic layer was distilled. There were isolated 32.2 grams of methyl isothiocyanate (B.P. 119° C, M.P. 35° C), corresponding to a yield of 98.6% of theory. The aqueous layer contained 0.477 mole of sodium chloride and 0.445 mole of sodium thiocyanate.

EXAMPLE 2

To 133.5 grams of a 43.2% N-methyl sodium dithiocarbamate solution (0.447 mole) in water there were added 17.9 grams of sodium hydroxide, 270 grams of water and 330 grams of methylene chloride. There were introduced under powerful stirring and cooling to 15° C within 25 minutes 0.469 mole of gaseous cyanogen chloride. This corresponds to a 5% excess. After the introduction the phases were separated immediately and there were isolated by distillation 31.5 grams of methyl isothiocyanate from the methylene chloride phase. This corresponded to a yield of 96.5% of theory.

EXAMPLE 3

There were dissolved in 250 grams of water 0.5 mole of potassium hydroxide, 0.5 mole of methyl amine added (as a 40% solution in water) and there were dropped in with stirring 0.5 mole of carbon disulfide. To the aqueous N-methyl potassium dithiocarbamate thus prepared there were added 250 grams of water, 0.5 mole of potassium hydroxide and 250 cc of methylene chloride. 0.516 mole of cyanogen chloride were led in under stirring and cooling. By distillation there were isolated from the methylene chloride phase 34.5 grams of methyl isothiocyanate, corresponding to a yield of 94.4% of theory.

EXAMPLE 4

A 35% aqueous solution of N-ethyl sodium dithiocarbamate was produced in known manner from 0.5 mole of sodium hydroxide, 0.5 mole ethyl amine and 0.5 mole of carbon disulfide in water. There were added 20 grams of sodium hydroxide, 220 cc water and 250 cc of methylene chloride. There were introduced at 16° C with stirring 0.515 mole of cyanogen chloride.

By distillation there were isolated from the organic solution 43.0 grams of ethyl isothiocyanate (B.P. 73° C/103 mm Hg). This corresponds to a yield of 98.8% of theory.

EXAMPLE 5

A 19.32% aqueous N-butyl sodium dithiocarbamate solution was produced from n-butyl amine, carbon disulfide and sodium hydroxide. 442.6 grams of this solution were treated with 20 grams of sodium hydroxide and 250 cc of methylene chloride. Under stirring and cooling to 12° C there were introduced within 30 minutes 0.510 mole of cyanogen chloride. After the phase separation there were isolated from the methylene chloride phase by distillation 54.3 grams of n-butyl isothiocyanate (B.P. 61.5°–62° C/14 mm Hg). This corresponds to a yield of 94.4% of theory.

EXAMPLE 6

In one hour 0.5 mole of cyclohexyl amine, 0.5 mole of sodium hydroxide and 60 grams of water were treated with 0.5 mole of carbon disulfide. The N-cyclohexyl sodium dithiocarbamate solution was stirred for a further hour at 50° C. There were added 1,000 cc of water, 20 grams of sodium hydroxide and 250 cc of methylene chloride. Under stirring there were led in at 6° C, 0.515 mol of cyanogen chloride. After the separation the methylene chloride layer was distilled. There were isolated 69.5 grams of cyclohexyl isothiocyanate (B.P. 98.5° C/13 mm Hg), corresponding to a yield of 98.4% of theory.

EXAMPLE 7

A 10.72% aqueous N-phenyl sodium dithiocarbamate solution was produced in known manner with 0.5 mole of aniline, 0.5 mole of sodium hydroxide, 0.5 mole of carbon disulfide and water. There were added 20 grams of sodium hydroxide and 250 cc of methylene chloride. Under stirring and cooling to 15° C there were introduced within 45 minutes 0.670 mole of gaseous cyanogen chloride. The reaction mixture was separated and the methylene chloride layer washed twice with 100 cc of water. It was subsequently distilled. There were obtained 61.2 grams of phenyl isothiocyanate (B.P. 93.5° C/14 mm Hg). This corresponds to a yield of 90.5% of theory.

EXAMPLE 8

There were added to 160 grams of a 40.4% aqueous N-methyl sodium dithiocarbamate solution (0.50 mole) 20 grams of sodium hydroxide, 250 grams of water and 300 grams of methylene chloride. Under stirring within 30 minutes there were introduced 0.55 mole of gaseous cyanogen chloride. The reaction temperature was allowed to increase to 35° C and the reaction mixture held at this temperature by water cooling. After the introduction of the cyanogen chloride the reaction mixture was cooled to room temperature and the two phases separated. There were isolated from the methylene chloride phase by distillation 32.7 grams of methyl isothiocyanate, corresponding to a yield of 89.4% of theory.

EXAMPLE 9

There were present in a round-bottomed flask 0.40 mole of N-methyl sodium dithiocarbamate as a 14.5% aqueous solution. To this aqueous solution there were added 0.40 mole of sodium hydroxide. 46.5 grams of cyanogen bromide were dissolved in 290 grams of methylene chloride and added to the aqueous phase within 30 minutes under stirring and cooling. The reaction temperature increased from 16° C to 24° C. The organic phase was separated and distilled. There were isolated 25.8 grams of methyl isothiocyanate (B.P. 119° C). This corresponds to a yield of 88.2% of theory.

What is claimed is:

1. A process of preparing isothiocyanates of the formula (I)

where R is (a) an alkyl group of 1 to 18 carbon atoms, (b) an alkyl group of 1 to 18 carbon atoms substituted with at least one —OH, —OR$^1$ or —SR$^1$ group where R$^1$ is alkyl of 1 to 6 carbon atoms or (c) cycloalkyl of 3 to 8 carbon atoms comprising reacting (1) a dithiocarbamate of the formula (II)

where Me is an alkali metal atom, a valence of an alkaline earth metal atom, ammonium or ammonium wherein at least one hydrogen is replaced by R with (2) a cyanogen halide in water, there being employed one mole of the dithiocarbamate of formula (II) as a 5 to 50% aqueous solution also including a base in the presence of an inert, water-immiscible organic solvent at a temperature of about −10° C to about +50° C with at least one mole of the cyanogen halide to form a water phase and an organic solvent phase, the isothiocyanate being in the organic phase.

2. The process of claim 1 wherein the cyanogen halide is cyanogen chloride or cyanogen bromide and there is included the step of separating the isothiocyanate from the organic phase.

3. The process of claim 2 wherein the cyanogen halide is cyanogen chloride.

4. The process of claim 2 wherein Me is an alkali metal, a valence of an alkaline earth metal or ammonium.

5. The process of claim 4 wherein the temperature is between about 0° C and 25° C.

6. The process of claim 2 wherein R is alkyl of 1 to 18 carbon atoms, alkyl of 1 to 18 carbon atoms substituted with —OR$^1$ or cycloalkyl of 3 to 8 carbon atoms.

7. The process of claim 6 wherein R is alkyl of 1 to 4 carbon atoms or cyclohexyl.

8. The process of claim 7 wherein R is methyl.

9. The process of claim 8 wherein the cyanogen halide is cyanogen chloride.

10. The process of claim 9 wherein the water immiscible solvent is methylene chloride.

11. A process according to claim 2 wherein the water immiscible solvent is a hydrocarbon, a halogenated hydrocarbon, a water insoluble ketone, a water insoluble ether, a water insoluble ester or nitrobenzene.

12. A process according to claim 11 wherein the solvent is a haloalkane.

13. A process according to claim 12 wherein the organic solvent is methylene chloride, chloroform or carbon tetrachloride.

14. A process according to claim 2 wherein there is employed more than one mole of cyanogen halide per mole of dithiocarbamate.

15. A process according to claim 14 wherein there is employed a 5 to 10% excess of cyanogen halide over the dithiocarbamate.

16. The process of claim 2 wherein R is an alkyl group of 1 to 18 carbon atoms.

17. The process of claim 2 wherein R is alkyl of 1 to 18 carbon atoms substituted with —OH, —OR$^1$ or —OSR$^1$.

18. The process of claim 2 wherein R is cycloalkyl of 3 to 8 carbon atoms.